United States Patent [19]

Duke et al.

[11] Patent Number: 4,855,446

[45] Date of Patent: Aug. 8, 1989

[54] PROCESS FOR THE RESOLUTION OF RACEMATES USING LACTONE ESTERS

[75] Inventors: Colin C. Duke, Dee Why; Robert J. Wells, Cromer, both of Australia

[73] Assignee: The Sherwin Williams Company, Cleveland, Ohio

[21] Appl. No.: 682,139

[22] Filed: Dec. 17, 1984

Related U.S. Application Data

[62] Division of Ser. No. 353,755, Mar. 1, 1982, Pat. No. 4,501,908.

[30] Foreign Application Priority Data

Mar. 12, 1981 [GB] United Kingdom ............... 8107737
Feb. 8, 1982 [GB] United Kingdom ............... 8203596

[51] Int. Cl.$^4$ .............. C07D 209/82; C07D 307/91; C07D 321/00; C07D 57/00
[52] U.S. Cl. ..................................... 548/444; 549/43; 549/285; 549/305; 549/314; 549/318; 549/461; 562/401; 562/402
[58] Field of Search ............... 549/305, 43, 314, 285, 549/318, 461, 333; 548/444; 562/401, 402

[56] References Cited

U.S. PATENT DOCUMENTS 3,185,710 5/1965 Dunkel et al. ............... 562/401 X
4,201,874 5/1980 Anderson et al. ............. 562/598
4,236,026 12/1980 Naumann ...................... 562/401

OTHER PUBLICATIONS

Chem Abstracts, vol. 70, paragraph 3199c (1969).
Organic Chemistry vol. II, 1968, FINAR, pp. 74-79.

Primary Examiner—Natalie Trousof
Assistant Examiner—Vera C. Clarke
Attorney, Agent, or Firm—Robert E. McDonald

[57] ABSTRACT

Racemic carboxylic acids are resolved into their enantiomers using optically active enantiomers of four lactones as resolving agents. The four lactones are 2,3-isopropylidene-ribonic acid-1,4-lactone, 1,2-isopropylidene-glucofuranurono-3,6-lactone, 2-hydroxy-3,3-dimethyl-1,4-butyrolactone and 3,4-isopropylidene-arabino-1,5-lactone. Novel diastereoisomeric esters of the acids with the lactones are disclosed.

15 Claims, No Drawings

PROCESS FOR THE RESOLUTION OF RACEMATES USING LACTONE ESTERS

This is a division of application Ser. No. 353,755, filed Mar. 1, 1982.

DISCUSSION OF PRIOR ART

The present invention relates to a process for the resolution of racemic carboxylic acids into their optically active enantiomers.

The resolution of racemic carboxylic acids is necessary where the properties of the individual optically active enantiomers are to be investigated. This is of particular value where the racemic acids show some biological activity, e.g. pharmaceutical or insecticidal activity, since the biological activity may vary greatly as between the individual optically active enantiomers.

It has previously been proposed to resolve racemic carboxylic acids using suitable optically active amines or chiral alcohols as the resolving agents. The use of amines suffers from the disadvantage that the conditions required for hydrolysis of the amide bond can cause partial or complete racemisation. Furthermore, few chiral alcohols have been reported which form esters which are readily resolved, e.g. by crystallization or chromatography.

SUMMARY OF INVENTION

It has now been found that four specific lactones readily form esters with racemic carboxylic acids whereby the said lactone esters are readily susceptible to separation into their enantiomers. The enantiomeric acids are obtainable in good yield and a high state of purity using the resolving agents of the instant invention.

According to the present invention therefore there is provided a process for the resolution of racemic carboxylic acids into their optically active enantiomers, which is characterized in that an optically active enantiomer of 2,3-isopropylidene-ribonic acid-1,4-lactone; 1,2-isopropylidene-glucofuranurono-3,6-lactone; 2-hydroxy-3,3-dimethyl-1,4-butyrolactone or 3,4-isopropylidene-arabino-1,5-lactone is used as the resolving agent.

Preferred resolving agents are D(−)-2-hydroxy-3,3-dimethyl-1,4-butyrolactone; 1,2-isopropylidene-(+)-α-D-glucofuranurono-3,6-lactone; 2,3-isopropylidene-D(+)-ribonic acid-1,4-lactone and 3,4-isopropylidene-L-arabino-1,5-lactone.

DETAILED DESCRIPTION OF THE INVENTION

The resolution method according to the present invention involves forming an ester of the racemic carboxylic acid with the lactone to yield a mixture of diastereoisomers. This mixture of diastereoisomers is then separated by physical means into the two optically active diastereoisomers. Following this, the optically active enantiometric acid may be regenerated from the ester formed.

The ester may be formed by any convenient method. One suitable method involves formation of the acid chloride of the racemic carboxylic acid followed by reaction of the lactone resolving agent with the acid chloride. This reaction is conveniently carried out in an inert aprotic solvent such as tetrahydrofuran and in the presence of a base such as pyridine.

Separation of the resulting mixture of diastereoisomers into the pure optically active diastereoisomers may be effected by any convenient means. It has been found that using the four lactone resolving agents of the present invention resolution of the mixture of diastereoisomeric esters into the individual optically active diastereoisomers can be readily achieved, e.g. by using crystallization or chromatography. Crystallization is the preferred method in view of its comparative simplicity. In the process of the present invention a solvent comprising ethyl acetate and hexane was successfully used in several instances but other solvents or solvent systems may also be employed. The chromatography method used may conveniently be high performance liquid chromatography carried out on silica gel. The preferred eluant for the chromatography is an ethyl acetate/hexane solvent system preferably containing the solvents in the ratio of 1:3 or 1:4.

Subsequent to the separation of the mixture of diastereoisomeric lactone esters into the optically active enantiomers thereof, the ester may be hydrolysed to the acid. This may be accomplished by any convenient hydrolysis method, e.g. using base catalysed hydrolysis. Care must be taken that the hydrolysis conditions are not so vigorous as to cause the optically active enantiomeric acid to revert to a racemic mixture. In many cases the hydrolysis may be carried out using aqueous hydrochloric acid or aqueous sodium hydroxide solution preferably as a 10% solution thereof.

The resolving agents of the instant invention are known compounds. D(−)- and L(+)-2-hydroxy-3,3-dimethyl-1,4-butyrolactones are also known under the names D(−) and L(+) pantolactone and are readily available articles of commerce. 1,2-Isopropylidene-(+)-α-D-glucofuranurono-3,6-lactone and the corresponding L(−) compound may be prepared according to the method of J. Chem. Soc. 339 (1941). The corresponding L(−) compound may also be prepared from L-glucose. According to an alternative method of preparation oxidation of D-glucose with air in the presence of either platinum (Heyns and R. Heinemann Ann., 1947, 558, 187) or palladium (M. Busch, G.P., 702, 729/1941) gave D-glucuronic acid, Evaporation of an aqueous solution of D-glucuronic acid yields crystalline D-glucofuranurono-6,3-lactone (F. Smith, J. Chem. Soc., 1944, 584; A Baeyer, Ann., 1870, 155, 257). 2,3-Isopropylidene-D(+)-ribonic acid-1,4-lactone may be prepared from D(+)-ribonic acid-1,4-lactone according to the method of Can. J. Chem. 1958 36 1720 and the corresponding L(−) ribonic acid lactone is readily prepared from L-arabinose by conversion to potassium L-arabonate as described in Biochem. J. 1965 94 75 and subsequent reaction with 2,2-dimethoxypropane. 3,4-Isopropylidene-L-arabino-1,5-lactone may be prepared from potassium L-arabonate via L-arabonic acid. The corresponding D compound may also be prepared by conventional methods, e.g. using the same method of preparation as for the L form and selective recrystallisation.

The process of the present invention is applicable generally to racemic carboxylic acids which are capable of forming lactone ester derivatives. Examples of such carboxylic acids include amino acids, mercapto carboxylic acids, cycloalkyl acids, aralkyl acids and heterocyclic acids wherein the heteroatom is nitrogen, oxygen or sulfur. The process of the invention may for example be employed to resolve acids of insecticidal ester such as those disclosed in German Patent Specification No. 2653189.

Such acids are cyclopropane compounds of the general formula

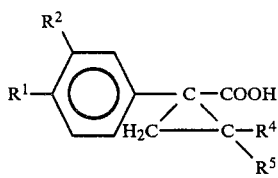

in which $R^1$ represents hydrogen or a $C_1$–$C_9$ alkoxy group, a $C_1$–$C_9$ alkylthio group, fluoro, chloro, bromo, a $C_1$–$C_9$ alkyl group, a nitro or amino group, $R^2$ represents hydrogen or a $C_1$–$C_9$ alkyl group or $R^1$ and $R^2$ together represent a methylenedioxy group and $R^4$ and $R^5$ are the same or different and represent fluoro, bromo, chloro or a $C_1$–$C_9$ alkyl group. The $C_1$–$C_9$ alkyl group means branched or unbranched alkyl groups such as methyl, ethyl, propyl, butyl, pentyl, heptyl and the like. $C_1$–$C_9$ alkoxy group means groups in which alkyl is as previously defined.

Specific examples of insecticidal acids which normally exist as racemic mixtures and which may conveniently be resolved into their enantiomers by the process of the present invention include:
cis-3-(2,2-dichlorovinyl)-2,2-dimethyl-cyclopropane carboxylic acid;
cis/trans-3-(2,2-dichlorovinyl)-2,2-dimethyl-cyclopropane carboxylic acid;
cis-3-(2,2-dibromovinyl)-2,2-dimethyl-cyclopropane carboxylic acid;
3-(1,2-dibromo-2,2-dichloroethyl)-2,2-dimethyl-cyclopropane carboxylic acid;
2,2-dimethyl-3-(2,2,2-trichloroethyl)-cyclopropane carboxylic acid;
2,2-dimethyl-4,5-benzospiro[2,4]-hepta-4,6-diene-1-carboxylic acid;
cis-3-(Z-2-chloro-3,3,3-trifluoroprop-1-enyl)-2,2-dimethyl-cyclopropane carboxylic acid;
2-(2-chloro-α,α,α-trifluoro-p-toluidino)-3-methyl lactic acid;
2-(4-chlorophenyl)-3-methyl lactic acid;
2-(4-chlorophenoxy)-3-methylbutanoic acid;
2-(4-difluoromethoxyphenyl)-3-methyl lactic acid;
1-(4-ethoxyphenyl)-2,2,3,3-tetrafluorocyclobutane carboxylic acid;
1-(4-bromophenyl)-2,2,3,3-tetrafluorocyclobutane carboxylic acid;
1-(4-ethoxyphenyl)-2,2-dichlorocyclopropane carboxylic acid;
1-(4-chlorophenyl)-2,2,3,3-tetrafluorocyclobutane carboxylic acid;
1-(3,4-methylenedioxyphenyl)-2,2,3,3-tetrafluorocyclobutane carboxylic acid;
2,2-dimethyl-3-(2,2-dichlorovinyl)-cyclopropane carboxylic acid and
1,4,5,6,7,7-hexachloro-8,9,10-trinorborn-5-ene-2-carboxylic acid.

The process of the invention may further be employed in the resolution of pharmaceutically active racemic carboxylic acids such as the acidic dibenzofuran derivatives, dibenzothiophene derivatives and carbazoles of the respective formulae I of U.K. patent specifications Nos. 1,385,620, 1,471,847 and B 1,572,358.

Specific examples of such pharmaceutically active racemic carboxylic acids include those specifically listed in the three patent specifications mentioned above and in particular 6-chloro-α-methyl-carbazole-2-acetic acid and 8-chloro-α-methyl-3-dibenzofuran acetic acid.

The lactone esters formed by reaction between the four lactones used as resolving agents according to the present invention and optically active carboxylic acids are novel compounds and constitute a further important aspect of the present invention.

Also according to the present invention therefore there are provided diastereoisomeric esters of an optically active enantiomer of 2,3-isopropylidene-ribonic acid-1,4-lactone, 1,2-isopropylidene-glucofuranurono-3,6-lactone 2-hydroxy-3,3-dimethyl-1,4-butyrolactone or 3,4-isopropylidene-arabino-1,5-lactone and an optically active carboxylic acid, said acid being either in racemic form or as a single optically active enantiomer thereof.

Preferred esters according to the present invention are those formed by reaction between the four lactone resolving agents employed according to the present invention and the specific carboxylic acids hereinbefore referred to, in particular those possessing pharmaceutical properties or being useful for the preparation of corresponding insecticidal esters.

The invention will now be illustrated with reference to the following Examples. The temperatures are given in degrees Centigrade.

EXAMPLE 1

(a) 10 g of racemic 1-(4-ethoxyphenyl)-2,2,3,3-tetrafluorocyclobutane carboxylic acid and 20 ml of thionyl chloride were heated under reflux for 1 hour and the excess thionyl chloride removed in vacuo. The residue was dissolved in dry tetrahydrofuran (50 ml), 6.5 g of 2,3-isopropylidene-D(+)-ribonic acid-1,4-lactone added and the stirred solution cooled in ice during the addition of pyridine (3 ml). The mixture was allowed to stand at room temperature overnight. The solvents were removed in vacuo and the residue partitioned between ethyl acetate (150 ml) and water (150 ml). The ethyl acetate layer was washed with 1M hydrochloric acid (2×100 ml), 5% sodium carbonate (1×50 ml) and brine (2×100 ml) and dried (Na$_2$SO$_4$). Concentration gave a crude mixture of the S(+) and R(−) diastereoisomeric esters of 1-(4-ethoxyphenyl)-2,2,3,3-tetrafluorocyclobutane carboxylic acid and 2,3-isopropylidene-D(+)-ribonic acid-1,4-lactone (15.5 g).

(b) These S(+) and R(−) diastereoisomeric esters were dissolved in a mixture of ethyl acetate and hexane (1:7, 120 ml) and cooled to give 5.4 g of fine colourless needles of the ester of S(+)-1-(4-ethoxyphenyl)-2,2,3,3-tetrafluorocyclobutane carboxylic acid which was 92% pure by high performance liquid chromatographic analysis. Recrystallization from ethyl acetate-hexane gave 4.4 g of the pure S(+)-ester, mp 108°–109°. $[\alpha]_D^{30} +39.0°$ (c=1.3, CHCl$_3$). $^1$H n.m.r. δ 7.03, 2H, d, J, 9 Hz; 6.72, 2H, d, J 9 Hz; 4.51, 1H, m; 4.2, 3H, m; 4.00, 1H, m; 3.90, 2H, J 7 Hz, q; 3.4, 1H, m; 2.85, 1H, m; 1.38, 3H, s; 1.37, 3H, t, J 7 Hz; 1.26, 3H, s. Mass spectrum: M+ 462.1296 C$_{21}$H$_{22}$F$_4$O$_7$ requires 462.1299. The combined mother liquors were chromatographed on silica gel using ethyl acetate-hexane (1:4) to give 6 g of the pure R(−)-lactone ester, 830 mg of mixed S(+) and R(−) diastereoisomers and a further 860 mg of the pure S(+)-lactone ester. The R(−)-lactone ester crystallized slowly from ether-hexane as large colourless prisms, mp 70°–71°. $[\alpha]_D^{29} -70.9°$ (c=1.3, CHCl$_3$). $^1$H n.m.r. δ 7.10, 2H, d, J 9 Hz; 6.85, 2H, d, J 9 Hz; 4.65, 1H, m; 4.52, 2H, AB, J 16, 4 Hz; 4.32, 2H, m; 3.99, 2H, q, J 7 Hz; 1.44, 3H, s; 1.38, 3H, t, J 7 Hz; 1.33, 3H, s. Mass spectrum: Measured M+ 462.1296, C$_{21}$H$_{22}$F$_4$O$_7$ requires 462.1299.

(c) The pure S(+)-lactone ester (4.5 g) was dissolved in methanol 50 ml and 10% aqueous sodium hydroxide (9 ml) added. The mixture was heated to 80° until homogeneous and allowed to stand at room temperature overnight. The mixture was acidified to pH 2 with 2M hydrochloric acid and stirred for 2 hours to yield a crystalline solid. This solid was extracted into dichloromethane. The dichloromethane extract washed with water, dried (MgSO$_4$) and concentrated to give 2.83 g of colourless crystalline S(+)-1-(4-ethoxyphenyl)-2,2,3,3-tetrafluorocyclobutane carboxylic acid, mp 89°–91°. $[\alpha]_D^{29} +93.7°$ (c=1, EtOH). The $^1$H n.m.r. spectrum was identical to that of the racemic acid.

(d) Treatment of the R(−)-lactone ester (112 mg) as described above in Example 1 (c) gave R(−)-1-(4-ethoxyphenyl)-2,2,3,3-tetrafluorocyclobutane carboxylic acid as a colourless crystalline solid (71 mg), mp 89°–90°, $[\alpha]_D^{28} -94.7°$ (c=1.41, CHCl$_3$). The $^1$H n.m.r. spectrum was identical to that of the racemic acid.

EXAMPLE 2

(a) The racemic acid 1-(4-ethoxyphenyl)-2,2,3,3-tetrafluorocyclobutane carboxylic acid (0.5 g ) was dissolved in benzene (8 ml) and thionyl chloride (1 ml) added and the mixture refluxed for 2 hours. The solvent and excess reagent was removed under reduced pressure and the pale yellow liquid dried under high vacuum. To this liquid was added a benzene (8 ml)-tetrahydrofuran (1 ml) solution of 1,2-isopropylidene (+)-α-D-glucofuranurono-3,6-lactone (410 mg) and pyridine (0.5 ml.). The mixture was allowed to stand for 2 hours during which time a crystalline solid formed. Completion of the reaction was checked using thin layer chromatography (silica gel, petroleum spirit:ethyl acetate 3:1). The reaction mixture was mixed with methylene chloride and washed with water. Concentration of the dried organic phase gave a very pale syrup (927 mg). The product was further purified by preparative layer chromatography (silica gel, petroleum spirit:ethyl acetate 3:1). In the $^1$H n.m.r. spectrum the two diastereoisomeric esters were observed to be present in a ratio of approximately 1:1 as measured from the doublets of proton-5 (δ 5.98 and 5.90) of the sugar moiety.

(b) A portion of the product from Example 2 (a) (412 mg) was dissolved in methanol (10 ml) and water added until the solution was slightly cloudy. Large colourless needle-like crystals of the ester of R(−) 1-(4-ethoxyphenyl)-2,2,3,3-tetrafluorocyclobutane carboxylic acid and 2,3-isopropylidene (+) α-D-glucofuranurono-3,6-lactone rapidly formed. These were filtered and washed with methanol-water and dried under vacuum (92.3 mg, mp. 142°–4°, $[\alpha]_D^{26} +14,7°$ (c=2.15 CHCl$_3$). The $^1$H n.m.r. spectrum showed a single doublet at δ 5.90 for proton-5 of the sugar moiety. Mass spectrum: M+ 490.1245. C$_{22}$H$_{22}$F$_4$O$_8$ requires M+ 490.1248. Major fragment ions m/e 475.274 (base), 247, 246, 219, 218.

(c) The acid chloride of racemic 1-(4-ethoxyphenyl)-2,2,3,3-tetrafluorocyclobutanoic acid was prepared by refluxing the acid (50 g) with thionyl chloride (100 ml) for 1.5 hours. Excess thionyl chloride was removed in vacuo, the residue dissolved in tetrahydrofuran (100 ml) and 1,2-isopropylidene(+)-α-D-glucofuranurono-3,6-lacetone (41 g) added and the solution stirred until homogeneous. The mixture was cooled in ice, pyridine (20 ml) added with stirring over 15 minutes and stirring continued at 20° for 3 hours. The mixture was partitioned between ethyl acetate (750 ml) and water (700 ml), the ethyl acetate layer washed with 1M aqueous hydrochloric acid (2×200 ml), 5% aqueous sodium carbonate (1×300 ml) and water (1×300 ml). Evaporation of the dried (MgSO$_4$) ethyl acetate layer gave a semisolid residue to which methanol (500 ml) was added causing partial dissolution to give a highly crystalline precipitate of 80% pure ester of S(+) 1-(4-ethoxyphenyl)-2,2,3,3-tetrafluorocyclobutane carboxylic acid and 1,2-isopropylidene (+) α-D-glucofuranurono-3,6-lactone (34 g) which was removed by vacuum filtration. Recrystallization from methanol yielded pure S(+)-ester, m.p. 178°–9°, $[\alpha]_D^{30} +79.0$ (c=1.5, CHCl$_3$). The $^1$H n.m.r. spectrum showed a single doublet at δ 5.98 with no doublet at δ 5.90 (cf $^1$H n.m.r. of R(−)-ester). Mass spectrum: Measured M+ 490.1245, C$_{22}$H$_{22}$F$_4$O$_8$ requires M+ 490.1248.

(d) A portion of the product of Example 2 (b) (43 mg) was dissolved in ethanol (5 ml) and a few drops of 1M aqueous sodium hydroxide were added. After a few hours the brown solution was acidified with aqueous hydrochloric acid and partitioned between water and methylene chlorie. Concentration of the organic phase gave a pale yellow syrup (25.5 mg). Purification by preparative thin layer chromatography (silica gel, petroleum spirit:ethyl acetate 4:1) gave R(−) 1-(4-ethoxyphenyl)-2,2,3,3-tetrafluorocyclobutane carboxylic acid ethyl ester as a colourless liquid (20.7 mg, $[\alpha]_D^{26} -80.1°$ (c=1.38, CHCl$_3$). The ethyl ester (20.7 mg) was dissolved in methanol (1 ml) and 10% aqueous sodium hydroxide (2 ml) added and the mixture was heated on the steam bath for a few minutes until homogeneous. After standing (3 hours) the homogeneous solution was acifified with aqueous hydrochloric acid and extracted with methylene chloride. The methylene chloride phase was dried and concentrated to give R(−) 1-(4-ethoxyphenyl)-2,2,3,3-tetrafluorocyclobutane carboxylic acid as a colourless crystalline solid (17.0 mg), $[\alpha]_D^{28} -98.7°$ (c=1.13, CHCl$_3$). The $^1$H n.m.r. spectrum was identical to that of the racemic acid.

(e) A portion of the S(+)-ester product of Example 2 (c) (1 g) was dissolved in methanol (20 ml) and 1M aqueous sodium hydroxide added. The mixture was heated at 60° until no longer turbid and allowed to stand at 20° overnight. Concentrated hydrochloric acid was added to the stirred solution to pH 2 followed by ethyl acetate (20 ml) and the mixture stirred for 2 hours. The ethyl acetate layer was extracted with 1M aqueous sodium hydroxide (2×15 ml) and the basic extracts combined and acidified with hydrochloric acid, the precipitated S(+)-1-(4-ethoxyphenyl)-2,2,3,3-tetrafluorocyclobutane carboxylic acid filtered, washed with water and dried. Recrystallization from hexane gave the pure (S+)-acid m.p. 89°-91°, $[\alpha]_D^{29} +98.0°$ (c=0.9, CHCl$_3$).

EXAMPLE 3

1.0 g of racemic 1-(4-chlorophenyl)-2,2,3,3-tetrafluorocyclobutane carboxylic acid was converted to a mixture of the S(+) and R(−) diastereoisomeric esters by conversion to the acid chloride and reaction with 0.7 g of 2,3-isopropylidene-D(+)-ribonic acid-1,4-lactone according to the general method of Example 1 (a) to yield 1.55 g of a gum which was crystallised from ethyl acetate-hexane to give the R(−)-diastereoisomeric lactone ester (0.5 g) which was then recrystallized from ethyl acetate-hexane to give pure material mp 123°-6°. The R(−) lactone ester had an $[\alpha]_D^{30} -69.1°$ (c=1.4, CHCl$_3$). $^1$H n.m.r. spectrum: δ (CDCl$_3$) 7.34, 2H, d, J 9 Hz; 7.14, 2H, d, J 9 Hz; 4.68, 1H, m; 4.56, 2H, s; 4.35, 2H, m; 3.50, 1H, m; 2.96, 1H, m; 1.44, 3H, s; 1.35, 3H, s. Mass spectrum: Measured M+ −15 437.0410; C$_{18}$H$_{14}$$^{35}$ClF$_4$O$_6$ requires M+ −15 437.0412. The combined mother liquors were dissolved in a mixture of ethyl acetate and hexane and chromatographed on silica gel using ethyl acetate-hexane (1:4) to give the R(−)-lactoneester of 1-(4-chlorophenyl)-2,2,3,3-tetrafluorocyclobutane carboxylic acid and 2,3-isopropylidene-D(+)-ribonic acid-1,4-lactone (200 mg), a mixture of diastereoisomers (82 mg) and the corresponding S(+)-isomer (650 mg) as an oil, $[\alpha]_D^{29} +34.0°$ (c=1.2, CHCl$_3$), $^1$H n.m.r. spectrum: δ (CDCl$_3$) 7.38, 2H, d, J 9 Hz; 7.22, 2H, d, J 9 Hz; 4.65, 1H, m; 4.2, 4H, m; 3.5, 1H, m; 3.0, 1H, m; 1.42, 3H, s; 1.32, 3H, s. Mass spectrum: Measured M+ 452.0656; C$_{19}$H$_{17}$ $^{35}$ClF$_4$O$_6$ requires 452.0647.

Hydrolysis of the two isomeric ribonyl esters prepared as described above gave R(−)-1-(4-chlorophenyl)-2,2,3,3-tetrafluorocyclobutane carboxylic acids as colourless crystals from hexane, mp 126°-8°, $[\alpha]_D^{26} -104°$ (c=1.8, CHCl$_3$) with the $^1$H n.m.r. spectrum identical to that of the racemic acid and the corresponding S(+)-acid with mp 122°-4°, $[\alpha]_D^{30} +108°$ (c=1.15, CHCl$_3$) with a $^1$H n.m.r. spectrum identical to that of the racemic acid.

EXAMPLE 4

The mixed diastereoisomeric esters of racemic 1-(4-bromophenyl)-2,2,3,3-tetrafluorocyclobutane carboxylic acid and 2,3-isopropylidene-D(+)-ribonic acid-1,4-lactone were prepared from the racemic acid (1.15 g) and the lactone using the general method of Example 1 (a) to yield 1.48 g of ester which was recrystallised from ethyl acetate-hexane to give 0.6 g of the R(−)-ester which, on a second recrystallization from ethyl acetate-hexane, gave colourless needles (0.52 g). The combined mother liquors were chromatographed on silica gel (ethyl acetate:hexane, 1:4) to yield the R(−)-ester (0.16 g), a mixed fraction (0.10 g) and the S(+)-ester as a viscous oil (0.67 g). R(−)-ester, mp 134°-5°, $[\alpha]_D^{30} -64.7°$ (c=1.8, CHCl$_3$). $^1$H n.m.r. spectrum: δ (CDCl$_3$) 7.45, 2H, d, J 9 Hz; 7.05, 2H, d, J 9 Hz; 4.64, 1H, m; 4.52, 2H, s; 4.29, 2H, m; 3.45, 1H, m; 2.92, 1H, m; 1.45; 3H, s; 1.35, 3H, s. Mass spectrum: M+ −15 480.9906; C$_{18}$H$_{14}$Br$^{79}$O$_6$F$_4$ requires 480.9908. S(+)-ester, a colourless gum $[\alpha]_D^{28}+29.5$) (c=1.5, CHCl$_3$). $^1$H n.m.r. spectrum: δ (CDCl$_3$) 7.44, 2H, d, J 9 Hz; 7.08, 2H, d, J 9 Hz; 4.62, 1H, m; 4.30, 4H, m; 3.45, 1H, m; 2.90, 1H, m; 1.43, 3H, s; 1.32, 3H, s. Mass spectrum: Measured M+ −15, 481.9901; C$_{18}$H$_{14}$$^{79}$BrO$_6$F$_4$ requires 481.9908. Hydrolysis of the R(−)-ester using the general method of Example 1 (d) gave the R(−)-acid as colourless prisms after recrystallization from hexane, mp. 121°-123°, $[\alpha]_D^{28} -89.5°$ (c=1, CHCl$_3$) (reported mp 24.5°, $[\alpha]_D^{22} -94.2°$ (EtOH) with the $^1$H n.m.r. spectrum identical to that of the racemic acid. Hydrolysis of the S(+)-ester (84 mg) using the general method of Example 1 (d) gave the S(+)-acid (50 mg) as colourless prisms after recrystallization from hexane, m.p. 122°-124°$[\alpha]_D^{28} +90.6°$ (c=1.3, CHCl$_3$) [reported m.p. 132°-133°$[\alpha]_D^{22} +93.85°$ (EtOH)] with the $^1$H n.m.r. spectrum identical to that of the racemic acid.

EXAMPLE 5

Mixed diastereoisomeric esters were prepared from 1-(3,4-methylenedioxyphenyl)-2,2,3,3-tetrafluorocyclobutane carboxylic acid (0.5 g) and 2,3-isopropylidene-D(+)-ribonic acid-1,4-lactone (0.35 g) using the general method of Example 1 (a) to yield 0.8 g of ester which was separated into its pure diastereoisomers by chromatography on silica gel, using ethyl acetate-hexane (1:3). The less polar R(−) diastereoisomeric ester (350 mg) was obtained as a solid foam, $[\alpha]_D^{29} -64.6°$ (c=0.8, CHCl$_3$). $^1$H n.m.r. spectrum: δ (CDCl$_3$) 6.76, 3H, m; 5.96, 2H, s; 4.70, 1H, m; 4.60, 1H, d, J 6 Hz; 4.50, 1H, d, J 6 Hz; 4.36, 2H, apparent d, J 2 Hz; 3.4, 1H, bm; 2.9, 1H, bm; 1.44, 3H, s; 1.36, 3H, s. Mass spectrum: Measured M+ 462.0932; C$_{20}$H$_{18}$F$_4$O$_8$ requires M+ 462.0935. The more polar S(+) diastereoisomeric ester crystallized from ethyl acetate-hexane as colourless needles, mp 107°-110°, $[\alpha]_D^{28} +39.3°$ (c=1.4°, (CHCl$_3$). $^1$H n.m.r. spectrum δ (CDCl$_3$) 6.76, 3H, m; 5.97, 2H, s; 4.64, 1H, m; 4.4, 2H, bs; 4.40, 1H, d, J 6 Hz; 4.21, 1H, d, J 6 Hz; 3.4, 1H, bm; 2.9, 1H, bm; 1.42, 3H, s; 1.30, 3H, s. Mass spectrum: Measured M+ 462.0932, C$_{20}$H$_{18}$F$_4$O$_8$ requires M+ 462.0935. Hydrolysis of the R(−) diastereoisomeric ester according to the general method of Example 1 (d) gave R(−)-1-(3,4-methylenedioxyphenyl)-2,2,3,3-tetrafluorocyclobutane carboxylic acid, mp 166°-169°, $[\alpha]_D^{28} -89.5°$ (c=1, CHCl$_3$). Hydrolysis of the S(+) diastereoisomeric ester (43 mg) according to the general method of Example 1 (d) gave S(+)-1-(3,4-methylenedioxyphenyl)-2,2,3,3-tetrafluorocyclobutane carboxylic acid (22 mg), m.p. 117°-123°, $[\alpha]_D^{28} +101.0°$ (c=1, CHCl$_3$).

EXAMPLE 6

B 1-(4-Ethoxyphenyl)-2,2-dichlorocyclopropane carboxylic acid (1 g) was esterified to its mixed diastereoisomers by conversion to the acid chloride and reaction with 2,3-isopropylidene-D(+)-ribonic acid-1,4-lactone (0.71 g) according to the general method of Example 1 (a) to yield 1.53 g of esters. A portion of this product was separated by preparative high performance liquid chromatography (silica gel; ethyl acetate:hexane, 1:3) (10 mg injections) to give two pure diastereoisomers as colourless viscous gums. The more polar isomer had $[\alpha]_D^{29} -51.3°$ (c=0.6, CHCl$_3$). $^1$H n.m.r. spectrum: δ (CDCl$_3$) 7.25, 2H, d, J 9 Hz; 6.86, 2H, d, J 9 Hz; 4.64, 1H, m; 4.50, 1H, d, J 6 Hz; 4.32, 3H, m; 4.00, 2H, q, J 6 Hz; 2.56, 1H, d, J 8 Hz; 2.00, 1H, d, J 7 Hz; 1.46, 3H, s; 1.40, 3H, t, J 7 Hz; 1.35, 3H, s.

The less polar isomer had $^1$H n.m.r. spectrum: δ (CDCl$_3$) 7.27, 2H, d, J 9 Hz; 6.88, 2H, d, J 9 Hz; 4.64, 1H, m; 4.35, 3H, m; 4.04, q, J 7 Hz; 3.90, d, J 6 Hz; 2.59, d, J 7 Hz; 1.99, d, J 7 Hz; 1.40, 3H, s; 1.40, 3H, t, J 7 Hz; 1.26, 3H, s. Hydrolysis of the more polar ester gave S(+)-1-(4-ethoxyphenyl)-2,2-dichlorocyclopropane carboxylic acid, mp 168°-169°, $[\alpha]_D^{27} +80.7°$ (c=0.9, CHCl$_3$. The less polar ester gave R(−)-1-(4-ethoxyphenyl)-2,2-dichlorocyclopropane carboxylic acid m.p. 167°-169°, $[\alpha]_D^{27} -99.2°$ (c=1, CHCl$_3$). The $^1$H n.m.r. spectra of both enantiomers were identical to that of the racemate.

EXAMPLE 7

Mixed diastereoisomeric esters were prepared by the general method of Example 1 (a) from 6-chloro-α-methyl-carbazole-2-acetic acid (1.35 g) and 2,3-isopropylidene-D(+)ribonic acid-1,4-lactone (0.94 g) to give 1.97 g of product. A portion of this product was separated by chromatography on silica gel (ethyl acetate: hexane, 1:2) to yield the less polar (−) diastereoisomeric ester as a white solid, mp 132°-134°, $[\alpha]_D^{28} -3.4°$ (c=1.4, CHCl$_3$). The more polar (+) diastereoisomeric ester crystallized from ethyl acetate-hexane as fine needles, mp 144°-7°, $[\alpha]_D^{30} +2.8°$ (c=1.2, CHCl$_3$). Slow evaporation of a solution of the mixed diastereoisomeric esters in ethyl acetate-hexane gave pure crystals of the more polar (+)diastereoisomeric ester. Hydrolysis of the more polar (+) diastereisomeric ester gave (−)-6-chloro-α-methyl-carbazole-2-acetic acid, $[\alpha]_D^{28} -42.3°$ (c=0.9, CH$_3$COCH$_3$).

EXAMPLE 8

Racemic 8-Chloro-α-methyl-3-dibenzofuanacetic acid (2.7 g) and 2,3-isopropylidene-D(+)-ribonic acid-1,4-lactone (1.88 g) gave, by the general method of Example 1 (a), 4.03 g of mixed diastereoisomeric esters which were readily separated by silica gel chromatography (ethyl acetate: hexane, 1:3) to yield the less polar (−) isomer (1.96 g) as a colourless gum $[\alpha]_D -34.9°$ (c=1, CHCl$_3$); partial $^1$H n.m.r. spectrum:δ (CDCl$_3$) 1.53, 3H, d, J 8 Hz; 1.32, 3H, s; 1.01, 3H, s) and the more polar isomer as a colourless solid which was crystallized from ether-hexane to yield needles, mp 111°-112°, $[\alpha]_D -14.9°$ (c=1, CHCl$_3$); partial $^1$H n.m.r. spectrum: δ (CDCl$_3$) 1.56, 3H, d, J 8 Hz; 1.37, 3H, s; 1.24, 3H, s.

EXAMPLE 9

To a solution of 2,3-isopropylidene-D(+)-ribono-1,4-lactone (1.88 g) in dry tetrahydrofuran (10 ml) was added 2-chloropropionyl chloride (1.27 g) followed by dry pyridine (0.79 g). Pyridine hydrochloride was immediately precipitated and, after standing at room temperature for 1 hour, the reaction mixture was diluted with diethyl ether (20 ml). The ethereal solution was partitioned with 1M HCl (2×10 ml), water (2×10 ml) and then dried over magnesium sulfate. Removal of the ether in vacuo gave a crystalline solid (2.8 g), part of which was resolved into two pure diastereoisomers by high performance liquid chromatography (ethyl acetate: hexane, 1:1). The less polar diastereoisomer was recrystallized from ether-hexane to give colourless prisms, mp 54.2°-55°, $[\alpha]_D^{28} -59.8°$ (c=1, CHCl$_3$). $^1$H n.m.r. spectrum: δ (CDCl$_3$) 4.80, 3H, m; 4.35, 3H, m; 1.67, 3H, d, J 8 Hz; 1.48, 3h, s; 1.40, 3H, s. Mass spectrum: M$^+$ −15, 263; C$_{10}$H$_{12}$Cl0$_6$ requires 263. The more polar isomer was recrystallized from diethyl ether-hexane to give colourless prisms, mp 64.5°-65°, $[\alpha]_D^{28} -45.9°$ (c=1, CHCl$_3$). $^1$H n.m.r. spectrum:δ (CDCl$_3$) 4.80, 3H, m; 4.40, 3H, m; 1.68, 3H, d, J 8 Hz; 1.48, 3H, s; 1.40, 3H, s.

EXAMPLE 10

A solution of 2,3-isopropylidene-D(+)-ribono-1,4-lactone (188 mg) and 2-phenylbutyric anhydride (310 mg) in d$_5$-pyridine (0.35 ml) was monitored by $^1$H n.m.r. until reaction was complete (1.5 hours). The mixture was dissolved in diethyl ether (20 ml), partitioned with aqueous hydrochloric acid (2×20 ml, 1M) and aqueous sodium hydroxide (2×10 ml, 1M). The combined alkaline extracts were acidified with 10M hydrochloric acid to pH 2, extracted with diethyl ether (2×10 ml) and the dried (MgSO$_4$) ether extracts concentrated in vacuo to give (+)2-phenylbutyric acid (150 mg), $[\alpha]_D^{25} +31°$ (c=1.0, benzene).

EXAMPLE 11

A mixture of racemic cis, trans-2,2-dimethyl-3-(2,2-dichlorovinyl)-cyclopropane carboxylic acids (2.09 g) was reacted with 2,3-isopropylidene-D(+)-ribonic acid-1,4-lactone (1.88 g) using the general method of Example 1 (a) to give a mixture of four esters (3.7 g). This mixture was allowed to stand at room temperature for 5 days during which time it crystallized. The solid mass triturated with diisopropyl ether (20 ml) and the undissolved solid collected by filtration to yield an approximately 1:1 mixture of the esters of the cis and trans (−)-1S-acids (1.2 g). A further portion of this mixture was separated by high performance liquid chromatography on silica gel into pure trans-(−)-1S and cis-(+)-1R esters (ethylacetate-hexane, 1:2.5). A portion of the mother liquors was also separated under the same conditions to give pure samples of the four esters.

The cis-(+)-1R ester crystallized from diisopropyl ether-hexane as colourless plates, mp 121.5°-123°, $[\alpha]_D^{25} -35.7°$ (c=1, CHCl$_3$). $^1$H n.m.r. spectrum: δ (CDCl$_3$) 6.10, 1H, d, J 8 Hz; 4.70, 3H, m; 4.28, 2H, m; 2.07, dd, J 8,8 Hz; 1.72, 1H, d, J=8 Hz; 1.48, 3H, s; 1.40, 3H, s; 1.24, 6H, s. The trans-(+)-1R ester crystallized from diisopropyl ether-hexane as colourless prisms, mp 89.5°-91°; $[\alpha]_D^{28} -48.8°$ (c=1, CHCl$_3$). $^1$H n.m.r. spectrum: δ (CDCl$_3$) 5.56, 1H, d, J 8 Hz; 4.64, 3H, m; 4.30, 2H, m; 2.20, 1H, dd, J 8, 6 Hz; 1.54, 1H, d, J 6 Hz; 1.47, 3H, s; 1.38, 3H, s; 1.24, 3H, s; 1.18, 3H, s. The cis-(−)-1S ester crystallized from diisopropyl ether as needles, mp 129°-134°, $[\alpha]_D^{25} -33.3°$ (c=1, CHCl$_3$). $^1$H n.m.r. spectrum: δ (CDCl$_3$) 6.08, 1H, d, J 8 Hz; 4.70, 3H, m; 4.24, 2H, m; 2.07, 1H, dd, J 8, 8 Hz; 1.72, 1H, d, J 8 Hz; 1.48, 3H, s; 1.38, 3H, s; 1.25, 6H, s. The trans-(−)-1S ester crystallized from diisopropyl ether-hexane as colourless needles mp 101.5°-103°, $[\alpha]_D^{26} -27.6°$ (c=1, CHCl$_3$). $^1$H n.m.r. spectrum: δ (CDCl$_3$) 5.56, 1H, d, J 8 Hz; 4.70, 3H, m; 4.28, 2H, apparent d, J 2 Hz; 2.10, 1H, dd, J 8, 6 Hz; 1.48, 3H, s; 1.38, 3H, s; 1.26, 3H, s; 1.19, 3H, s.

EXAMPLE 12

Racemic 1-(4-ethoxyphenyl)-2,2,3,3-tetrafluorocyclobutane carboxylic acid (10 g) and thionyl chloride (5 ml) was heated under reflux for 2 hours and excess thionyl chloride removed in vacuo. The residue was dissolved in dry tetahydrofuran (25 ml), 4.45 g of D(−)-pantolactone added and the stirred solution cooled in ice during the addition of pyridine (3 ml). The mixture was allowed to stand at room temperature for 2 hours. The solvents were removed in vacuo and the residue was chromatographed on silica gel using ethyl acetate-hexane (1:5) to give 5.3 g of the R (−)-lactone ester of 1-(4-ethoxyphenyl)-2,2,3,3-tetrafluorocyclobutane carboxylic acid and D(−)-pantolactone, 2.9 g of mixed diastereoisomeric lactone esters (∼1:2 (−):(+)) and 4.3 g of the corresponding S (+)-lactone ester. The R (−)-lactone ester crystallized on standing and was recrystallized from hexane as large needles, mp 73°-4°; $[\alpha]_D^{28} -59.3°$ (c=1.7, CHCl$_3$); $^1$H n.m.r. spectrum: δ (CDCl$_3$) 7.20, 2H, d, J 9 Hz; 6.85, 2H, d, J 9 Hz; 5.23, 1H, s; 3.98, 2H, q, J 7 Hz; 3.94, 2H, s; 3.45, 1H, m; 3.05, 1H, m; 1.38, 3H, t, J 7 Hz; 1.16, 3H, s; 1.06, 3H, s. Mass spectrum: M$^+$ 404.1237; C$_{19}$H$_{20}$O$_5$F$_4$ requires 404.1244. The S (+)-lactone ester was a colourless syrup; $[\alpha]_D^{28} +71.0°$ (c=1.5, CHCl$_3$); $^1$H-n.m.r. spectrum: δ (CDCl$_3$) 7.20, 2H, d, J 9 Hz; 6.85, 2H, d, J 9 Hz; 5.20, 1H, s; 3.98, 2H, q, J 7 Hz; 3.88, 2H, s; 3.45, 1H, m; 3.05, 1H, m; 1.38, 3H, t, J 7 Hz; 1.02, 3H, s; 0.89, 3H, s. The R(−)-ester (3.55 g) was mixed with methanol (10 ml) and 10% aq. NaOH (7 ml) and stirred overnight to give a homogeneous solution. After dilution with water (75 ml) the solution was acidified with 2M aq. HCl and extracted with $CH_2Cl_2$ gave a colourless crystalline solid (2.53 g), $[\alpha]_D^{29} - 88.8°$ (c=1.3, EtOH) with a $^1H$ n.m.r. spectrum identical to the racemic acid. The S(+)-ester (3.76 g) was treated as above to give a colourless crystalline solid (2.43 g), $[\alpha]_D^{29} + 91.0°$ (c=1.6, $CHCl_3$) with a $^1H$ n.m.r. spectrum identical to the racemic acid.

EXAMPLE 13

1-(4-Ethoxyphenyl)-2,2-dichlorocyclopropane carboxylic acid (10 g) was heated with thionyl chloride (5 ml) for 1.5 hours and the excess thionyl chloride removed in vacuo. To the residue was added a solution of D(−)-pantolactone (5 g) in dry tetrahydrofuran (20 ml) followed by pyridine (4 ml). The mixture was allowed to stand at room temperature for 2 hours and was then partitioned between benzene (100 ml) and 1M aqueous hydrochloric acid (100 ml). The benzene layer was then washed with water (100 ml), 10% aqueous sodium carbonate (100 ml) and water (100 ml), then dried over magnesium sulfate. Concentration gave the crude mixture of diastereoisomeric lactone esters of 1-(4-ethoxyphenyl)-2,2-dichlorocyclopropane carboxylic acid and D(−)-pantolactone (13.74 g). The diastereoisomeric lactone esters were dissolved in hexane and cooled to give dense crystals (5.43 g) of the lactone ester of S(+)-1-(4-ethoxyphenyl)-2,2-dichlorocyclopropane carboxylic acid of greater than 90% purity. Recrystallization from hexane gave the pure S(+)-lactone ester, mp 118°; $[\alpha]_D^{26} + 84.2°$ (c=1.2, $CHCl_3$); $^1H$ n.m.r. spectrum: δ ($CDCl_3$) 7.32, 2H, d, J 9 Hz; 6.83, 2H, d, J 9 Hz; 5.25, 1H, s; 3.98, 2H, q, J 7 Hz; 3.92, 2H, s; 2.61, 1H, d, J 8 Hz; 2.05, 1H, d, J 8 Hz; 1.38, 3H, t, J 7 Hz; 1.05, 3H, s; 0.87, 3H, s. Mass spectrum: M+ 386.0682; $C_{18}H_{20}O_5Cl_2^{35}$ requires 386.0687. The mother liquors from the crystallization of the S (+)-lactone ester were partially concentrated and on standing at room temperature gave colourless needles (3.76 g) of the lactone ester of R(−)-1-(4-ethoxyphenyl)-2,2-dichlorocyclopropane carboxylic acid of greater than 90% purity. Recrystallization from hexane gave pure R (−)-lactone ester, mp 95°–6°; $[\alpha]_D^{28} - 72.0°$ (c=1.0, $CHCl_3$); $^1H$ n.m.r. spectrum: δ ($CDCl_3$) 7.32, 2H, d, J 9 Hz; 6.84, 2H, d, J 9 Hz, 5.27, 1H, s, 4.00, 2H, q, J 7 Hz; 3.97, 2H, s; 2.61, 1H, d, J 8 Hz, 2.08, 1H, d, J 8 Hz; 1.37, 3H, t, J 7 Hz; 1.19, 3H, s; 1.14, 3H, s. Mass spectrum: M+ 386.0678; $C_{18}H_{20}O_5Cl_2^{35}$ requires 386.0687. The R(−)-ester (3.40 g) was mixed with methanol (15 ml) and 10% aq. NaOH (10 ml) and heated at 100° until homogeneous. After standing overnight, water (100 ml) was added and the mixture was acidified with 1M aq. HCl and extracted with $CH_2Cl_2$. Concentration of the $CH_2Cl_2$ gave a colourless crystalline solid (2.54 g) $[\alpha]_D^{28} - 83.5°$ (c=1, $CHCl_3$) with a $^1H$ n.m.r. spectrum identical to the racemic acid.

EXAMPLE 14

To a solution of the D(−)-pantolactone (0.7 g) in tetrahydrofuran (5 ml) was added 2-chloropropionyl chloride (0.7 g) followed by dry pyridine (0.5 ml). Pyridine hydrochloride was immediately precipitated and, after standing for 1.5 hours, the reaction mixture was filtered and the filtrate on concentration gave the crude mixture of diastereoisomeric lactone esters. The mixture of diastereoisomeric lactone esters was chromatographed on silica gel using ethyl acetate-hexane (1:3) to give 0.18 g of the less polar diastereoisomeric lactone ester, 0.97 g of a mixture of the two diastereoisomeric lactone esters and 0.015 g of the more polar diastereoisomeric lactone ester. The less polar diastereoisomeric lactone ester was a colourless liquid; $[\alpha]_D^{27} + 13.8°$ (c=0.8, $CHCl_3$); $^1H$ n.m.r. spectrum: δ ($CDCl_3$) 5.34, 1H, s; 4.50, 1H, q, J 7 Hz; 4.02, 2H, s; 1.73, 3H, d, J 7 Hz; 1.24, 3H, s; 1.16, 3H, s. The more polar diastereoisomeric lactone ester was a colourless liquid; $[\alpha]_D^{27} - 3.5°$ (c=1.5, $CHCl_3$); $^1H$ n.m.r. spectrum: δ ($CDCl_3$) 5.31, 1H, s; 4.50, 1H, q, J 7 Hz; 4.03, 2H, s; 1.75, 3H, d, J 7 Hz; 1.23, 3H, s; 1.15, 3H, s. The lactone esters were hydrolysed using the general method of Example 1 (c) to give pure R(−)- and S(+)-2-chloropropionic acids.

EXAMPLE 15

Trans-2,2-dimethyl-3-(2,2-dichlorovinyl)-cyclopropane carboxylic acid (0.8 g) and thionyl chloride (0.5 ml) were heated at 100° for 1.5 hours and excess thionyl chloride removed in vacuo. D(−)-pantolactone (0.5 g) dissolved in dry tetrahydrofuran was added to the resulting acid chloride followed by pyridine (0.4 ml). After 2 hours the reaction mixture was partitioned between benzene (20 ml) and 1M aqueous hydrochloric acid and the organic layer washed with water (20 ml), 10% aqueous sodium carbonate (20 ml) and water (20 ml) then dried with magnesium sulfate. The solvents were removed in vacuo and the residue dissolved in diisopropyl ether. On standing at room temperature colourless plates (0.50 g) of the lactone ester of the R(+)-trans-2,2-dimethyl-3-(2,2-dichlorovinyl) cyclopropane carboxylic acid formed which were 84% pure. Recrystallization from diisopropyl ether gave the pure R(+)-trans-lactone ester as colourless plates, mp 124°–5°; $[\alpha]_D^{27} + 1.2°$ (c=1, $CHCl_3$); $^1H$ n.m.r. spectrum: δ ($CDCl_3$) 5.62, 1H, d, J 8 Hz; 5.32, 1H, s; 4.00, 2H, s; 2.27, 1H, dd, J 8 Hz, J 5 Hz; 1.72, 1H, d, J 5 Hz; 1.35, 3H, s; 1.24, 6H, s; 1.15, 3H, s. Mass spectrum: M+ 320.0578; $C_{14}H_{18}O_4Cl_2^{35}$ requires 320.0581. Separation by preparative high performance liquid chromatography (ethyl acetate-hexane, 1:3) gave the S(−) trans-ester which was recrystallized from hexane to give colourless crystals, m.p. 68°–70°, $[\alpha]_D^{28} - 16.4°$ (c=1.1, $CHCl_3$). $^1H$ n.m.r. spectrum: 5.55, 1H, d, J 8 Hz; 5.28, 1H, s; 3.96, 2H, s; 2.28, 1H, dd, J 8 Hz, J 5 Hz; 1.72, 1H, d, J 5 Hz; 1.30, 3H, s; 1.22, 3H, s; 1.18, 3H, s; 1.09, 3H, s. Mass spectrum: M+ −35 285.0891; $C_{14}H_{18}O_4Cl^{35}$ requires 285.0892. The lactone ester was hydrolysed using the general method of Example 1 (c) to give pure R(+)-trans-2,2-dimethyl-3-(2,2-dichlorovinyl)-cyclopropane carboxylic acid.

EXAMPLE 16 cis-2,2-dimethyl-3-(2,2-dichlorovinyl)cyclopropane carboxylic acid (0.8 g) (containing 5% of the corresponding trans acid as an impurity) was converted to a crude mixture of diastereoisomers using the general method of Example 15. The mixture (1.19 g) was dissolved in hexane and on standing at room temperature gave colourless needles (0.25 g) of the lactone ester of R(+)-cis-2,2-dimethyl-3-(2,2-dichlorovinyl)cyclopropane carboxylic acid containing 17% of the R(+)-trans-ester as an impurity. Separation by preparative high performance liquid chromatography (ethyl acetate:hexane 1:4) gave the R(+) cis lactone ester which was recrystallized from hexane as colourless needles, m.p. 109°, $[\alpha]_D^{27} + 35.7°$ (c=0.6, $CHCl_3$), $^1H$ n.m.r. spectrum: δ (CDCl₃) 6.10, 1H, d, J 8 Hz; 5.25, 1H, s; 3.96, 2H, s; 2.08, 1H, dd, J 8 Hz, J 8 hz; 1.95, 1H, d, J 8 Hz; 1.29, 3H, s; 1.26, 3H, s; 1.18, 3H, s; 1.10, 3H, s. Mass spectrum: M+ −35, 285.0893; C₁₄H₁₈O₄Cl³⁵ requires 285.0892. Separation by preparative high performance liquid chromatography (ethyl acetate-hexane, 1:3) gave the S(−)-cis-ester which was isolated as a colourless liquid containing 15% of the mixed trans-esters [α]$_D^{27}$−12.1° (c=1.8, CHCl₃), ¹H n.m.r. spectrum: δ (CDCl₃) 6.17, 1H, d, J 8 Hz; 5.29, 1H, s; 4.00, 2H, s; 2.14, 1H, s; 1.97, 1H, d, J 8 Hz; 1.30, 3H, s; 1.26, 3H, s; 1.20, 3H, s; 1.10, 3H, s. Mass spectrum: M+ 320.0581; C₁₄H₁₈O₄Cl₂³⁵ requires 320.0581. The lactone ester was hydrolysed using the general method of Example 1 (c) to give pure R(+)-cis-2,2-dimethyl-3-(2,2-dichlorovinyl)-cyclopropane carboxylic acid.

EXAMPLE 17

Cis,trans-2,2-dimethyl-3-(2,2-dichlorovinyl)cyclopropane carboxylic acid (3.3 g) (cis:trans 2:3) was converted to a crude mixture of diastereoisomers (5.0 g) (cis:trans 1:2 by ¹H n.m.r.) using the general method of Example 15. The mixture (5 g) was dissolved in diisopropyl ether, filtered through celite and the filtrate concentrated to 25 ml and 25 ml of hexane added. Cooling to 0° gave pale brown mica-like plates (1.4 g) consisting of the R(+) trans ester 80% and the R(+) cis ester (20%).

EXAMPLE 18

(a) 1,4,5,6,7,7-Hexachloro-8,9,10-trinorborn-5-ene-2-carboxylic acid (10 g) was heated with thionyl chloride (10 ml) for 1.5 hours at 100° and the excess reagent was removed under vacuo. To the residue was added a tetrahydrofuran (50 ml) solution of 2,3-isopropylidene-D(+)-ribonic acid-1,4-lactone (5.46 g) and then pyridine (3 ml) was added slowly to the solution. A colourless crystalline solid formed and the mixture was left standing for 3 hours. The mixture was filtered and the crystals washed with tetrahydrofuran and the filtrate evaporated under reduced pressure and the residue mixed with ethyl acetate and washed with 1M aqueous hydrochloric acid saturated with sodium chloride and then saturated aqueous sodium chloride and the ethyl acetate phase was evaporated under reduced pressure. The residue was subjected to column chromatography on silica gel (Merck Kieselgel H) using ethyl acetate:hexane (1:4) to separate the two diastereoisomeric lactone esters of 2,3-isopropylidene-D(+)-ribonic acid-1,4-lactone and of 1,4,5,6,7,7-hexachloro-8,9,10-trinorborn-5-ene-2-carboxylic acid: the (−)-lactone-ester (5.03 g) mixed diastereoisomeric lactone esters (0.41 g) and the (+)-lactone-ester (3.77 g).

(b) The crystalline (−)-lactone ester was recrystallized from hexane-ethyl acetate to give colourless plates (4.69 g), mp 129°–133°, [α]$_D^{29}$−47.3° (c=2.8, CHCl₃). ¹H n.m.r. spectrum: δ (CDCl₃) 4.92, 1H, d, J 6 Hz; 4.76, 2H, m; 4.46, 1H, dd, J 12 Hz, J 2.5 Hz; 4.20, 1H, dd, J 12 Hz, J 2.5 Hz; 3.58, 1H, dd, J 5 Hz, J 8 Hz; 2.62, 2H, m; 1.49, 3H, s; 1.40, 3H, s. Mass spectrum: measured M+ −15 496.8691; C₁₅H₁₁O₆Cl₆³⁵ requires 496.8687. The crystalline (+)-lactone ester was recrystallized from hexane-ethyl acetate to give colourless plates (3.41 g), mp 136°–143°, [α]$_D^{29}$+13.6° (c=2, CHCl₃). ¹H n.m.r. spectrum: δ (CDCl₃) 4.85, 1H, d, J 6 Hz; 4.73, 2H, m; 4.32, 2H, m; 3.60, 1H, dd, J 5 Hz, J 8 Hz; 2.62, 2H, m; 1.49, 3H, s; 1.40, 3H, s. Mass spectrum: measured M+ −15 496.8691; C₁₅H₁₁O₆Cl₆³⁵ requires 496.8687.

(c) The (−)-lactone ester (3.58 g) was dissolved in a mixture of methanol (25 ml) and 10% aqueous sodium hydroxide (7 ml). After standing overnight, water (150 ml) was added to give a homogeneous solution. On acidification with 1M hydrochloric acid a white solid precipitated (2.17 g) which was recrystallized from hexane to give colourless crystals of (−)-1,4,5,6,7,7-hexachloro-8,9,10-trinorborn-5-ene-2-carboxylic acid, mp 159°–186° decomp., [α]$_D^{29}$ (c=5.5, CHCl₃), ¹H n.m.r. spectrum identical to the racemic acid.

(d) The (+)-lactone ester (2.54 g) was dissolved in a mixture of methanol (15 ml) and 10% aqueous sodium hydroxide (5 ml). After standing overnight, water was added to give a homogeneous solution. On acidification with 1M aqueous hydrochloric acid a white solid precipitated (1.56 g) which was recrystallized from hexane to give colourless crystals of (+)-1,4,5,6,7,7-hexachloro-8,9,10-trinorborn-5-ene-2-carboxylic acid, m.p. 159°–186° decomp., [α]$_D^{29}$+10.0° (c=5.6, CHCl₃), ¹H n.m.r. spectrum identical to the racemic acid.

1,4,5,6,7,7-Hexachloro-8,9,10-trinorborn-5-ene-2-carboxylic acid may be prepared as follows:

A mixture of hexachloropentadiene (137.3 g) and methyl acrylate (43.3 g) was heated at 90°–95° for 24 hours with stirring under reflux to give methyl 1,4,5,6,7,7-hexachloro-8,9,10-trinorborn-5-ene-2-carboxylate (180.6 g) as a colourless liquid. ¹H n.m.r. spectrum: δ (neat) 3.67, 3H, s; 3.56, 1H, m; 2.58, 2H, m. Mass spectrum: measured M+ 355.8497; C₉H₆O₂Cl₆³⁵ requires 355.8497.

The methyl ester (180 g) was dissolved in methanol (625 ml) and 10% aq. Sodium hydroxide (530 ml) was added and the mixture was stirred overnight at room temperature to give a brown solution. Most of the methanol was removed by evaporation under reduced pressure and the aqueous residue was acidified with 2M HCl and extracted with CH₂Cl₂. Evaporation of the CH₂Cl₂ gave a crystalline residue of 1,4,5,6,7,7-hexachloro-8,9,10-trinorborn-5-ene-2-carboxylic acid which was recrystallized from hexane as colourless crystals (67 g) mp 156°–170° decomp. ¹H n.m.r. spectrum: δ (CDCl₃) 9.60, 1H, br.s; 3.65, 1H, dd, J 5 Hz, J 8 Hz; 2.65, 2H, m. Mass spectrum: measured M+ 341.8341; C₈H₄O₂Cl₆³⁵ requires 341.8340.

EXAMPLE 19

1,4,5,6,7,7-Hexachloro-8,9,10-trinorborn-5-ene-2-carboxylic acid (10 g) was heated with thionyl chloride (10 ml) at 100° for 1.5 hours and the excess thionyl chloride removed in vacuo. To the residual liquid was added a tetrahydrofuran (50 ml) solution of L(+)-pantolactone and pyridine (3.5 ml) added slowly to be stirred solution. After 3 hours the crystalline solid that had formed was filtered and washed with tetrahydrofuran and the filtrate concentrated under reduced pressure. The residue was mixed with benzene (200 ml) and washed with 1M aqueous hydrochloric acid, saturated with sodium chloride, saturated aqueous sodium chloride, 10% aqueous sodium carbonate and saturated aqueous sodium chloride. Removal of the solvent under reduced pressure gave a colourless syrup (12.32 g). Crystallization of the syrup from hexane-ethyl acetate (5:1) gave the separate diastereoisomeric esters of 1,4,5,6,7,7-hexachloro-8,9,10-trinorborn-5-ene-2-carboxylic acid and L(+)-2-hydroxy-3,3-dimethyl-1,4-butyrolactone. Initial crystallization of the diastereoisomeric esters gave large colourless needles of the (−)-ester and concentration of the filtrate gave large colourless hexagonal crystals of the (+)-ester. The colourless needles of the (−)-ester (4.81 g) had m.p. 152°-4°, $[\alpha]_D^{26}$ −10.0° (c=1.1, CHCl$_3$). $^1$H n.m.r. spectrum: δ (CDCl$_3$) 5.28, 1H, s; 4.03, 2H, 2; 3.77, 1H, dd, J 8 Hz, J 5 Hz; 2.70, 2H, m; 1.22, 3H, s, 1.14, 3H, s. Mass spectrum: measured M+, 453.8864; C$_{14}$H$_{12}$O$_4$Cl$_6{}^{35}$ requires 453.8865. Hydrolysis of the (−)-ester using the general method described in Example 18 gave the (−)-acid as colourless crystals.

The colourless hexagonal crystals of the (+)-ester (4.63 g) had m.p. 165°, $[\alpha]_D^{26}$ +20.0 (c=1.3, CHCl$_3$). $^1$H n.m.r.: δ (CDCl$_3$) 5.35, 1H, s; 4.04, 2H, s; 3.80, 1H, dd, J 8 Hz, J 5 Hz; 2.70, 2H, m; 1.25, 3H, s; 1.24, 3H, s. Mass spectrum: measured M+, 453.8860; C$_{14}$H$_{12}$O$_4$Cl$_6{}^{35}$ requires 453.8865. Hydrolysis of the (+)-ester using the general method described in Example 18 gave the (+)-acid as colourless crystals.

EXAMPLE 20

Racemic 1-(4-ethoxyphenyl)-2,2-dichlorocyclopropane carboxylic acid (10.0 g) and thionyl chloride (5 ml) were heated at 100° under reflux for 2 hours and the excess thionyl chloride removed in vacuo. To the residue was added a solution of L(+)-2-hydroxy-3,3-dimethyl-1,4-butyrolactone (5 g) in dry tetrahydrofuran (20 ml) followed by pyridine (4 ml). The mixture was allowed to stand at room temperature for 2 hours then was partitioned between benzene (100 ml), and 1M aqueous hydrochloric acid saturated with sodium chloride (100 ml). The benzene layer was then washed with saturated aqueous sodium chloride (100 ml), 10% aqueous sodium carbonate Na$_2$CO$_3$ (100 ml) and saturated aqueous sodium chloride (100 ml) then dried over magnesium sulfate. Concentration gave the crude mixture of diastereoisomeric lactone esters of 1-(4-ethoxyphenyl)-2,2-dichlorocyclopropane carboxylic acid and L(+)-2-hydroxy-3,3-dimethyl-1,4-butyrolactone (12.43 g). Crystallization from hexane gave colourless crystals of the R(−)-lactone ester (5.62 g) which were recrystallized from hexane-ethyl acetate to give colourless crystals (3.30 g), m.p. 119°, $[\alpha]_D^{26}$ −89.5° (c=1.2, CHCl$_3$). $^1$H n.m.r. spectrum identical to the (+) enantiomer given in Example 13. Crystallization of the concentrated filtrate gave colourless crystals of the S(+)-lactone ester (3.80 g), m.p. 96°, $[\alpha]_D^{28}$ +77.1° (c=1.4, CHCl$_3$). $^1$H n.m.r. spectrum identical to the (−) enantiomer given in Example 13. The R(−)-lactone ester (3.30 g) was mixed with methanol (15 ml) and 10% aq. NaOH (10 ml) and heated at 100° until homogeneous. After standing overnight water (100 ml) was added and the mixture was acidified with 1M aqueous hydrochloric acid and extracted with methylene dichloride. Concentration of the methylene dichloride gave colourless crystalline solid R(−)-1-(4-ethoxyphenyl)-2,2-dichlorocyclopropane carboxylic acid (2.20 g), $[\alpha]_D^{28}$ −96.6° (c=1.1, CHCl$_3$) with a $^1$H n.m.r. spectrum identical to that of the racemic acid. The S(+)-lactone ester (2.09 g) was treated as described above to give S(+)-1-(4-ethoxyphenyl)-2,2-dichlorocyclopropane carboxylic acid as a colourless crystalline solid (1.50 g), $[\alpha]_D^{28}$ +93.4° (c=1.8, CHCl$_3$) with a $^1$H n.m.r. spectrum identical to that of the racemic acid.

EXAMPLE 21

Racemic 1-(4-Bromophenyl)-2,2,3,3-tetrafluorocyclobutane carboxylic acid (1.0 g) and thionyl chloride (0.5 ml) were heated under reflux at 100° for 2 hours and the excess thionyl chloride removed in vacuo. The residue was dissolved in dry tetrahydrofuran (5 ml), L(+)-2-hydroxy-3,3-dimethyl-1,4-butyrolactone (0.4 g) was added and the solution cooled in ice during the addition of pyridine (0.4 ml). The mixture was allowed to stand at room temperature for 2 hours. The solvents were removed in vacuo and the residue chromatographed on silica gel using ethyl acetate-hexane (2:5) to give the mixed diastereoisomeric lactone esters of 1-(4-bromophenyl)-2,2,3,3-tetrafluorocyclobutane carboxylic acid and L(+)-2-hydroxy-3,3-dimethyl-1,4-butyrolactone (1.33 g). Crystallization from hexane gave colourless crystals of the S(+)-lactone ester (0.28 g), m.p. 121°-122°, $[\alpha]_D^{28}$ +60.3° (c=1.3, CHCl$_3$). $^1$H n.m.r. spectrum: δ (CDCl$_3$) 7.46, 2H, d, J 8 Hz; 7.22, 2H, d, J 8 Hz; 5.24, 1H, s; 3.95, 2H, s; 3.50, 1H, m; 3.00, 1H, m; 1.16, 3H, s; 1.07, 3H, s. Mass spectrum: measured M+, 438.0085; C$_{17}$H$_{15}$O$_4$Br$^{79}$F$_4$ requires 438.0087. Hydrolysis of the S(+)-lactone ester using the general method of Example 20 gave the S(+)-acid as colourless crystals. Crystallization of the concentrated filtrate gave colourless crystals of the R(−)-lactone ester, m.p. 58°-60°, $[\alpha]_D^{26}$ −59.5° (c=1,2 CHCl$_3$). $^1$H n.m.r. spectrum: 7.47, 2H, d, J 8 Hz; 7.19, 2H, d, J 8 Hz; 5.23, 1H, s; 3.95, 2H, s; 3.60, 1H, m; 3.50, 1H, m; 1.07, 3H, s; 0.93, 3H, s. Mass spectrum: measured M+, 438.0085; C$_{17}$H$_{15}$O$_4$Br$^{79}$F$_4$ requires 438.0087. Hydrolysis of the R(−)-lactone ester using the general method of Example 20 gave the R(−)-acid as colourless crystals.

EXAMPLE 22

Racemic 2-(4-Chlorophenoxy)-3-methylbutanoic acid (1.0 g) and thionyl chloride (1 ml) were heated under reflux at 100° for 2 hours and excess thionyl chloride removed in vacuo. The residue was dissolved in dry tetrahydrofuran (5 ml), L(+)-2-hydroxy-3,3-dimethyl-1,4-butyrolactone (0.65 g) was added and the solution cooled in ice during the addition of pyridine (0.5 ml). The mixture was allowed to stand at room temperature for 2 hours. The solvents were removed in vacuo and the residue chromatographed on silica gel using ethyl acetate-hexane (1:3) to give the mixed disasteroisomeric lactone esters (1.22 g), of 2-(4-chlorophenoxy)-3-methylbutanoic acid and L(+)-2-hydroxy-3,3-dimethyl-1,4-butyrolactone. Crystallization from hexane gave colourless crystals of the (−)-lactone ester (0.36 g), m.p. 137°-139°, $[\alpha]_D^{27}$ −59.2° (c=1, CHCl$_3$). $^1$H n.m.r. spectrum: δ (CDCl$_3$) 7.17, 2H, d, J 8 Hz; 6.82, 2H, d, J 8 Hz; 5.35, 1H, s; 4.47, 1H, d, J 5 Hz; 3.99, 2H, s; 2.35, 1H, m; 1.16-1.10, 12H, m. Mass spectrum: measured M+340.1077; C$_{17}$H$_{21}$O$_5$Cl$^{35}$ requires 340.1075. The (−)-lactone ester (0.18 g) was dissolved in methanol (1 ml) and 10% aqueous sodium hydroxide (0.5 ml) added and the mixture was heated at 50° for 2 hours. The solution was then diluted with water (20 ml), acidified with 1M aqueous hydrochloric acid and extracted with methylene chloride. Removal of the solvent in vacuo gave colourless solid crystals of (−)-2-(4-chlorophenoxy)-3-methylbutanoic acid, $[\alpha]_D^{26}$ −31.3° (c=1.6, CHCl$_3$). $^1$H n.m.r. spectrum identical to that of the racemic acid.

EXAMPLE 23

(a) Racemic 1-(4-ethoxyphenyl)-2,2,3,3-tetrafluorocyclobutane carboxylic acid (1.0 g) and thionyl chloride (1 ml) were heated under reflux at 100° for 2 hours and excess thionyl chloride removed in vacuo. The residue was dissolved in dry tetrahydrofuran (5 ml), 3,4-isopropylidene-L-arabino-1,5-lactone (0.64 g) was added and the solution cooled in ice during the addition of pyridine (0.5 ml). The mixture was allowed to stand at room temperature for 2 hours. The solvents were removed in vacuo and the residue chromatographed on silica gel using ethyl acetate-hexane (2:7) to give crystalline R(−)-lactone ester (0.63 g) and crystalline S(+)-lactone ester (0.48 g) of 1-(4-ethoxyphenyl)-2,2,3,3-tetrafluorocyclobutane carboxylic acid and 3,4-isopropylidene-L-arabino-1,5-lactose. Recrystallization of the R(−)-lactone ester from ethyl acetate-hexane gave colourless needles (0.29 g), m.p. 125°–126°, $[\alpha]_D^{29}$ −25.6° (c=2, CHCl$_3$). $^1$H n.m.r. spectrum: δ (CDCl$_3$) 7.20, 2H, d, J 8 Hz; 6.85, 2H, d, J 8 Hz; 5.33, 1H, m; 4.40, 4H, m; 3.98, 2H, q, J 7 Hz; 3.50, 1H, m; 3.00, 1H, m; 1.45, 3H, s; 1.43, 3H, t, J 7 Hz; 1.34, 3H, s. Mass spectrum: measured M+ 462.1296; C$_{21}$H$_{22}$O$_7$F$_4$ requires 462.1299. Recrystallization of the S(+)-lactone ester from ethyl acetate-hexane gave colourless needles (0.30 g), m.p. 114° $[\alpha]_D^{29}$ 79.1° (c=2.3, CHCl$_3$). $^1$H n.m.r. spectrum: δ (CDCl$_3$) 7.20, 2H, d, J 8 Hz; 6.85, 2H, d, J 8 Hz, 5.27, 1H, m; 4.34, 4H, m; 3.98, 2H, q, J 7 Hz; 3.50, 1H, m; 3.00, 1H, m; 1.45, 3H, t, J 7 Hz; 1.41, 3H, s; 1.29, 3H, s. Mass spectrum: measured M+ 462.1287; C$_{21}$H$_{22}$O$_7$F$_4$ requires 462.1299.

(b) The R(−)-lactone ester (85.4 mg) was dissolved in hot methanol (2 ml) and 10% aqueous sodium hydroxide (1 ml) added to give a homogeneous solution. Water (2 ml) was added to the solution and the homogeneous solution left standing overnight then water was added (50 ml). Acidification with 1M aqueous hydrochloric acid gave colourless crystals of R(−)-1-(4-ethoxyphenyl)-2,2,3,3-tetrafluorocyclobutane carboxylic acid (41.2 mg), $[\alpha]_D^{28}$ −82.3° (c=1.4, CHCl$_3$). $^1$H n.m.r. spectrum identical to the racemic acid.

(c) The S(+)-ester (93.4 mg) was treated as above to give colourless crystals of S(+)-1-(4-ethoxyphenyl)-2,2,3,3-tetrafluorocyclobutane carboxylic acid (44.4 mg), $[\alpha]_D^{28}$ +88.6° (c=1.5, CHCl$_3$). $^1$H n.m.r. spectrum identical to the racemic acid.

EXAMPLE 24

Potassium L-arabonate (11.4 g) (prepared by the method of P. Andrews, L. Hough and J. M. Picken, *Biochem. J.* 1965, 94, 75) was dissolved in a mixture of water (50 ml) and pyridine (5 ml) and heated at 135° for 3 hours in an autoclave. The reaction mixture was evaporated under reduced pressure to remove most of the pyridine and then passed through an ion-exchange column (H+ form). The acidic eluant was collected and concentrated to a brown syrup under vacuo and then dissolved in acetone (300 ml), 2,2-dimethoxypropane (10 ml) and sulphuric acid (0.2 ml) were added and the solution left standing overnight. The solvent was removed in vacuo and the residue chromatographed on silica gel using ethyl acetate:hexane (1:1) to give the crude crystalline product (0.76 g). Recrystallization from ethyl of acetate-hexane gave colourless crystals 2,3-isopropylidene L(−) ribonic acid-1,4-lactone (0.38 g), m.p. 137°–139°, $[\alpha]_D^{28}$ +71.1° (c=1.5, CHCl$_3$). $^1$H n.m.r. spectrum: δ (CDl$_3$) 4.75, 2H, m; 4.55, 1H, m; 3.85, 2H, m; 2.55, 1H, t, J 6 Hz; 1.45, 3H, s; 1.37, 3H, s. Mass spectrum: M+ 15 173 (90%), 129 (11), 85 (19), 59 (34), 43 (100).

EXAMPLE 25

Potassium L-arabonate (prepared by the method of P. Andrews, L. Hough and J. M. Picken, *Biochem. J.* 1965, 94, 75) was dissolved in water and passed through a Biorad AG50×8 200–400 mesh in ion-exchange column (H+ form). The acidic eluant was collected and concentrated to a colourless syrup of L-arabonic acid (14.75 g). The syrup was dissolved in acetone (300 ml) and sulphuric acid (0.5 ml) and cupric sulphate (31 g) was added and the mixture stirred at room temperature for 24 hours. Thin layer chromatography on silica gel (ethyl acetate solvent) indicated partial conversion to product. After neutralizing the acid with concentrated aqueous ammonia the mixture was filtered and the filtrate was concentrated in vacuo. The residue was chromatographed on silica gel using ethyl acetate:hexane (1:1) to give the crude crystalline product (4.87 g). Recrystallization from ethyl acetate-hexane gave colourless crystals of 3,4-isopropylidene-L-arabino-1,5-lactone (3.71 g), m.p. 96°–97°, $[\alpha]_D^{29}$ +2.8 (c=3, CHCl$_3$). $^1$H n.m.r. spectrum: 4.39, 5H, m; 3.60, 1H, d, J 3 Hz; 1.50, 3H, s; 1.37, 3H, s. Mass spectrum: measured M+ −15 173.0442; C$_7$H$_9$O$_5$ requires 173.0450.

What is claimed:

1. A process for the resolution of a racemic carboxylic acid selected from the group consisting of a compound of the formula:

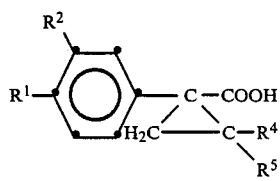

in which

R$^1$ represents hydrogen or a C$_1$–C$_9$ alkoxy group, a C$_1$–C$_9$ alkylthio group, fluoro, chloro, bromo, a C$_1$–C$_9$ alkyl group, a nitro or amino group, R$^2$ represents a hydrogen or a C$_1$–C$_9$ alkyl group or R$^1$ and R$^2$ together represents a methylenedioxy group and R$^4$ and R$^5$ are the same or different and represent fluoro, bromo, chloro, or a C$_1$–C$_9$ alkyl group;

cis-3-(2,2-dichlorovinyl)-2,2-dimethyl-cyclopropane carboxylic acid;

cis/trans-3-(2,2-dichlorovinyl)-2,2-dimethyl-cyclopropane carboxylic acid;

cis-3-(2,2-dibromovinyl)-2,2-dimethyl-cyclopropane carboxylic acid;

3-(1,2-dibromo-2,2-dichloroethyl)-2,2-dimethyl-cyclopropane carboxylic acid;

2,2-dimethyl-3-(2,2,2-trichloroethyl)-cyclopropane carboxylic acid;

2,2-dimethyl-4,5-benzospiro[2,4]-hepta-4,6-diene-1-carboxylic acid;

cis-3-(Z-2-chloro-3,3,3-trifluoroprop-1-enyl)-2,2-dimethylcyclopropane carboxylic acid;

2-(2-chloro-α,α,α-trifluoro-p-toluidino)-3-methyl lactic acid;

2-(4-chlorophenyl)-3-methyl lactic acid;

2-(4-chlorophenoxy)-3-methylbutanoic acid;

2-(4-difluoromethoxyphenyl)-3-methyl lactic acid;

1-(4-ethoxyphenyl)-2,2,3,3-tetrafluorocyclobutane carboxylic acid;

1-(4-bromophenyl)-2,2,3,3-tetrafluorocyclobutane carboxylic acid;

1-(4-chlorophenyl)-2,2,3,3-tetrafluorocyclobutane carboxylic acid;

1-(3,4-methylenedioxyphenyl)-2,2,3,3-tetrafluorcyclobutane carboxylic acid;

2,3-dimethyl-3-(2,2-dichlorovinyl)-cyclopropane carboxylic acid;
1,4,5,6,7,7-hexachloro-8,9,10-trinoborn-5-ene-2-carboxylic acid;
2-chloropropanoic acid;
2-phenylbutanoic acid;
6-chloro-α-methyl-carbazole-2-acetic acid; and
8-chloro-α-methyl-3-dibenzofuran acetic acid into its optically active enantiomers, which comprises forming a mixture of diastereomeric esters of the racemic carboxylic acid with a compound selected from the group consisting of an optically active enantiomer of 2,3-isopropylidene-ribonic acid-1,4-lactone;
1,2-isopropylidene-glucofuranurono-3,6-lactone,
2-hydroxy-3,3-dimethyl-1,4-butylrolactone and 3,4-isopropylidene-arabino-1,5-lactone separating the resulting mixture of diastereomeric esters into two optically active diastereomeric esters, and hydrolyzing the separated optically active diastereomeric esters to their corresponding acid.

2. The process of claim 1 wherein the diastereoisomeric esters are separated by crystallization or chromatography.

3. The process of claim 2 wherein the chromatography method used is high performance liquid chromatography.

4. The process of claim 1 wherein the resolving agent used is D(−)-2-hydroxy-3,3-dimethyl-1,4-butyrolactone.

5. The process of claim 1 wherein the resolving agent used is L(+)-2-hydroxy-3,3-dimethyl-1,4-butyrolactone.

6. The process of claim 1 wherein the resolving agent used is 1,2-isopropylidene-(+)-α-D-glucofuranurono-3,6-lactone.

7. The process of claim 1 wherein the resolving agent used is 1,2-isopropylene-(−)-α-L-glucofuranurono-3,6-lactone.

8. The process of claim 1 wherein the resolving agent used is 2,3-isopropylidene-D(+)-ribonic acid-1,4-lactone.

9. The process of claim 1 wherein the resolving agent used is 2,3-isopropylidene-L(−)-ribonic acid-1,4-lactone.

10. The process of claim 1 wherein the resolving agent used is 3,4-isopropylidene-L-arabino-1,5-lactone.

11. The process of claim 1 wherein the resolving agent used is 3,4-isopropylidene-D-arabino-1,5-lactone.

12. The process of claim 1 wherein the carboxylic acid has the formula

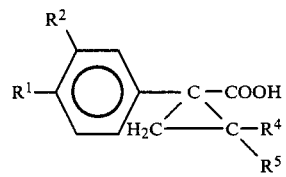

in which $R^1$ represents hydrogen or a $C_1$–$C_9$ alkoxy group, a $C_1$–$C_9$ alkylthio group, fluoro, chloro, bromo, a $C_1$–$C_9$ alkyl group, a nitro or amino group, $R^2$ represents hydrogen or a $C_1$–$C_9$ alkyl group or $R^1$ and $R^2$ together represents a methylenedioxy group and $R^4$ and $R^5$ are the same or different and represent fluoro, bromo, chloro or a $C_1$–$C_9$ alkyl group.

13. The process of claim 1 wherein the carboxylic acid is cis-3-(2,2-dichlorovinyl)-2,2-dimethyl-cyclopropane carboxylic acid;
cis/trans-3-(2,2-dichlorovinyl)-2,2-dimethyl-cyclopropane carboxylic acid;
cis-3-(2,2-dibromovinyl)-2,2-dimethyl-cyclopropane carboxylic acid;
3-(1,2-dibromo-2,2-dichloroethyl)-2,2-dimethyl-cyclopropane carboxylic acid;
2,2-dimethyl-3-(2,2,2-trichloroethyl)-cyclopropane carboxylic acid;
2,2-dimethyl-4,5-benzospiro[2,4]-hepta-4,6-diene-1-carboxylic acid;
cis-3-(Z-2-chloro-3,3,3-trifluoroprop-1-enyl)-2,2-dimethyl-cyclopropane carboxylic acid;
2-(2-chloro-α,α,α-trifluoro-p-toluidino)-3-methyl lactic acid;
2-(4-chlorophenyl)-3-methyl lactic acid;
2-(4-chlorophenoxy)-3-methylbutanoic acid;
2-(4-difluoromethoxyphenyl)-3-methyl lactic acid;
1-(4-ethoxyphenyl)-2,2,3,3-tetrafluorocyclobutane carboxylic acid;
1-(4-bromophenyl)-2,2,3,3-tetrafluorocyclobutane carboxylic acid;
1-(4-ethoxyphenyl)-2,2-dichlorocyclopropane carboxylic acid;
1-(4-chlorophenyl)-2,2,3,3-tetrafluorocyclobutane carboxylic acid;
1-(3,4-methylenedioxyphenyl)-2,2,3,3-tetrafluorocyclobutane carboxylic acid;
2,2-dimethyl-3-(2,2-dichlorovinyl)-cyclopropane carboxylic acid or
1,4,5,6,7,7-hexachloro-8,9,10-trinorborn-5-ene-2-carboxylic acid.

14. The process of claim 1 wherein the carboxylic acid is 6-chloro-α-methyl-carbazole-2-acetic acid.

15. The process of claim 1 wherein the carboxylic acid is 8-chloro-α-methyl-3-dibenzofuran acetic acid.

* * * * *